US009592060B2

(12) United States Patent
Pancholy

(10) Patent No.: US 9,592,060 B2
(45) Date of Patent: *Mar. 14, 2017

(54) METHOD OF TRANSRADIAL CATHETERIZATION, DEVICE FOR ULNAR ARTERY COMPRESSION, AND METHOD OF USE

(71) Applicant: Samir Bipin Pancholy, Clarks Summit, PA (US)

(72) Inventor: Samir Bipin Pancholy, Clarks Summit, PA (US)

(73) Assignee: VASOINNOVATIONS, INC., South Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/340,023

(22) Filed: Nov. 1, 2016

(65) Prior Publication Data

US 2017/0042552 A1 Feb. 16, 2017

Related U.S. Application Data

(63) Continuation of application No. 15/062,150, filed on Mar. 6, 2016, now Pat. No. 9,510,838, which is a (Continued)

(51) Int. Cl.
*A61B 17/132* (2006.01)
*A61B 17/135* (2006.01)

(52) U.S. Cl.
CPC ........ *A61B 17/1325* (2013.01); *A61B 17/135* (2013.01)

(58) Field of Classification Search
CPC ............ A61B 17/1285; A61B 17/1325; A61B 17/135; A61B 17/132; A61B 17/1322;
(Continued)

(56) References Cited

U.S. PATENT DOCUMENTS

| 37,156 A | 12/1862 | Dunton |
| 3,905,361 A | 9/1975 | Hewson et al. |

(Continued)

FOREIGN PATENT DOCUMENTS

| EP | 0 601 756 A1 | 6/1994 |
| WO | WO 97/02783 A1 | 1/1997 |

OTHER PUBLICATIONS

"Prevention of Radial Artery Occlusion: Prophylactic Hyperperfusion Evaluation Trial ( PROPHET-II)" ClinicalTrial.Gov, Protocol Registration System, Mar. 2012, by Pancholy.*

(Continued)

*Primary Examiner* — Kathleen Holwerda
*Assistant Examiner* — Socrates L Boutsikaris
(74) *Attorney, Agent, or Firm* — Rajendra G. Sardesai

(57) ABSTRACT

Disclosed are methods and devices for obtaining patent hemostasis of the radial artery by compressing the uninstrumented ulnar artery to increase radial artery flow. The device comprises a band having an inflatable bladder for applying blunt pressure to the ulnar artery. The method comprises applying a pressure to the homolateral ulnar artery and applying a pressure to the radial artery at the access site to obtain hemostasis at the access site.

17 Claims, 4 Drawing Sheets

Related U.S. Application Data continuation of application No. 13/941,219, filed on Jul. 12, 2013, now Pat. No. 9,308,000.

(58) Field of Classification Search
CPC ......... A61B 2017/00902; A61B 2017/120034; A61F 2013/00829
USPC .............. 606/201–203; 601/132, 151, 33, 40
See application file for complete search history.

(56) References Cited

U.S. PATENT DOCUMENTS

| | | | |
|---|---|---|---|
| 4,863,429 | A | 9/1989 | Baldwin |
| 4,920,971 | A | 5/1990 | Blessinger |
| 4,981,133 | A | 1/1991 | Rollband |
| 5,152,302 | A | 10/1992 | Fareed |
| 5,295,951 | A | 3/1994 | Fareed |
| 5,307,811 | A | 5/1994 | Sigwart et al. |
| 5,464,420 | A | 11/1995 | Hori et al. |
| 5,486,194 | A | 1/1996 | Kawasaki et al. |
| 5,496,262 | A | 3/1996 | Johnson et al. |
| 5,514,155 | A | 5/1996 | Daneshvar |
| 5,569,297 | A | 10/1996 | Makower et al. |
| 5,643,315 | A | 7/1997 | Daneshvar |
| 5,660,182 | A | 8/1997 | Kuroshaki et al. |
| 5,792,173 | A | 8/1998 | Breen et al. |
| 5,840,037 | A | 11/1998 | Tochikubo et al. |
| 6,007,562 | A | 12/1999 | Harren et al. |
| 6,336,901 | B1 | 1/2002 | Itonaga et al. |
| 6,361,496 | B1 | 3/2002 | Zikorus et al. |
| 6,527,727 | B2 | 3/2003 | Itonaga et al. |
| 6,694,821 | B2 | 2/2004 | Yamakoshi et al. |
| 6,827,727 | B2 | 12/2004 | Stalemark et al. |
| 7,498,477 | B2 | 3/2009 | Wada et al. |
| 7,927,295 | B2 | 4/2011 | Bates et al. |
| 8,034,009 | B2 | 10/2011 | Bates et al. |
| 8,152,776 | B2 | 4/2012 | McCluskey |
| 8,481,803 | B2 | 7/2013 | Wada et al. |
| 8,481,805 | B2 | 7/2013 | Wada et al. |
| 2002/0147404 | A1 | 10/2002 | Kato |
| 2003/0199922 | A1 | 10/2003 | Buckman |
| 2004/0049214 | A1 | 3/2004 | Akerfeldt |
| 2004/0098035 | A1 | 5/2004 | Wada et al. |
| 2004/0122469 | A1 | 6/2004 | Akerfeldt |
| 2005/0153090 | A1 | 7/2005 | Marchitto |
| 2009/0138039 | A1 | 5/2009 | Wada et al. |
| 2009/0281565 | A1 | 11/2009 | McNeese |
| 2012/0296369 | A1 | 11/2012 | Atthoff et al. |
| 2013/0116725 | A1 | 5/2013 | Wada et al. |
| 2013/0178894 | A1 | 7/2013 | Wada et al. |
| 2013/0289613 | A1 | 10/2013 | Wada |
| 2014/0142615 | A1 | 5/2014 | Corrigan, Jr. |
| 2015/0018869 | A1 | 1/2015 | Benz |

OTHER PUBLICATIONS

Patel, T. et al, "Contralateral transradial approach for carotid artery stenting: a feasibility study" J. Catheter Cardiovasc Interv. vol. 75(2), p. 268-75. Feb. 2010.
Pancholy, S. "Comparison of the effect of intra-arterial versus intravenous heparin on radial artery occlusion . . . " Am J Cardiol. vol. 104(8) p. 1083-5 Oct. 2009.
Pancholy, S. "Prevention of Radial Artery Occlusion:Prophylactic Hyperperfusion Evaluation Trial ( PROPHET-II)" ClinicalTrial. Gov, Protocol Registration System, Mar. 2012.
Pancholy, S. et al, "Subcutaneous administration of nitroglycerin to facilitate radial artery cannulation" Catheter Cardiovasc Interv. vol. 68(3) p. 389-9, Sep. 2006.
Mamas, M, "Dissection, Occlusion, and Spasm; Myths Involving Sheathless Guide Catheters" Catheterization and Cardiovascular Interventions 76:777-778, Feb. 2010.
Pancholy, S "Hemostasis and Radial Artery Patency", Presentation, http://www.slideshare.net/theradialist/pancholy-sb-201111, Jan. 2012.

Shroff, A et al "Comparing radial with femoral artery access in patients with ST-segment elevation myocardial infarction . . . " Expert Rev Cardio Ther. 11(5):525-7, May 2013.
Patel, T et al "Coronary cannulation through mirror-image right aortic arch during right transradial approach . . . " J Invasive Cardiol. 24(5):234-5, May 2012.
Kwan, T. et al "Balloon-assisted sheathless transradial intervention (BASTI) using 5 Fr guiding catheters" J Invasive Cardiol. 24(5):231-3, May 2012.
Dharma, S. et al "Nitroglycerin plus diltiazem versus nitroglycerin alone for spasm prophylaxis with transradial approach" J Invasive Cardiol. 24(3):122-5, Mar. 2012.
Pancholy, S et al "A technique to access difficult to find upper extremity veins for right heart catheterization . . . " Catheter Cardiovasc Interv., 78(5):809-12, Nov. 2011.
Patel, T et al, "Reaccessing an occluded radial artery: a "proximal entry" technique" J Interv Cardiol. 24(4):378-81, Aug. 2011.
Patel, T et al, "Management of radial and brachial artery perforations during transradial procedures . . . " J Invasive Cardiol. 21(10):544-7, Oct. 2009.
Patel, T et al, "A simple approach for the reduction of knotted coronary catheter in radial artery during transradial approach"J Invasive Cardiol. 23(5):E126-7, May 2011.
Samir Pancholy, et al, "Prevention of Radial Artery Occlusion—Patent Hemostasis Evaluation Trial (PROPHET study)" Catheterization and Cardiovascular Interv 72:335-340 (2008).
Samir B. Pancholy, "Transradial Access in an Occluded Radial Artery: New Technique" Journal Invasive Cardiology, vol. 19, Issue 12, Dec. 2007.
Samir B. Pancholy, "Transradial Approach" Angioplasty.Org Interview Series, 3 pages, Aug. 2008.
Samir B. Pancholy, "Impact of Two Different Hemostatic Devices on Radial Artery Outcomes after Transradial Catheterization" J Invasive Cardiology,vol. 21,Issue 3, Mar. 2009.
Ivo Bernat, et al, "Efficacy and Safety of Transient Ulnar Artery Compression to Recanalize Actute Radial Artery Occlusion . . . " Am J Cardiol,107:1698-1701 (2011).
Samir B. Pancholy, "Strategies to Prevent Radial Artery Occlusion After Transradial PCI" Curr Cardiol Rep, 16:505, Jun. 2014.
International Search Report in International application No. PCT/US 16/41801.
Written Opinion of the International Searching Authority in International application No. PCT/US 16/41801.
Search History in International application No. PCT/US 1641801.
Examiner's Search in priority U.S. Appl. No. 13/941,219, filed Jul. 12, 2013—Other References Patent.
Examiner's Search in priority U.S. Appl. No. 13/941,219, filed Jul. 12, 2013—Other References NPL.
Examiner's Search in priority U.S. Appl. No. 13/941,219, filed Jul. 12, 2013—Other References Inventor.
Patel, T. et al, "Balloon-assisted tracking: A must-know technique . . . " Cath. Cardio. Interv., Wileyonlinelibrary.com; DOI:10.1002/ccd.24959, Apr. 2013.
Kwan, T. et al, "Transulnar catheterization in patients with ipsilateral radial artery occlusion" Cath Cardio Interv, Wileyonlinelibrary.com, DOI 10.1002/ccd.24662 Sep. 2012.
Patel, T. et al, "Balloon-assisted tracking of a guide catheter . . . : A technical report" Cath. Cardio. Interv., Wileyonlinelibrary.com; DOI 10.1002/ccd.24504, May 2012.
Kwan, T. et al. "Feasibility and safety of 7F sheathless guiding catheter during transradial coronary intervention", Wileyonlinelibrary.com; DOI 10.1002/ccd.24310, Aug. 2012.
Pancholy, S et al, "Comparison of a priori versus provisional heparin therapy on radial artery occlusion (PHARAOH Study)", Am J Cardiol, vol. 110(2), p. 173-176 Jul. 2012.
Pancholy, S et al, "Radial artery access technique evaluation trial: randomized comparison . . . ", Catheter Cardiovasc Interv., vol. 80(2), p. 288-91, Aug. 2012.
Pancholy, S et al, "Effect of duration of hemostatic compression on radial artery occlusion after transradial access", Catheter Cardio Interv, vol. 79(1), p. 78-81, Jan. 2012.

(56) References Cited

OTHER PUBLICATIONS

Caputo, R, et al, "Transradial arterial access for coronary and peripheral procedures . . . " Catheter Cardiovasc Interv., vol. 78(6), p. 823-39, Nov. 2011.
Bertrand, O et al, "Transradial approach for coronary angiography and interventions . . . ", JACC Cardiovasc Interv., vol. 3(10), p. 1022-31 Oct. 2010.
Pancholy, S et al, "Comparison of door-to-balloon times for primary PCI using transradial versus transfemoral approach" Catheter Cardio Interv. vol. 75(7), p. 991-5 Jun. 2010.

* cited by examiner

METHOD OF TRANSRADIAL CATHETERIZATION, DEVICE FOR ULNAR ARTERY COMPRESSION, AND METHOD OF USE

CROSS-REFERENCE TO RELATED APPLICATIONS

This application is a continuation of co-pending U.S. patent application Ser. No. 15/062,150, filed Mar. 6, 2016, which is a continuation of U.S. patent application Ser. No. 13/941,219, filed Jul. 12, 2013, now U.S. Pat. No. 9,308,000 issued Apr. 12, 2016.

BACKGROUND OF INVENTION a. Field of Invention

The invention relates generally to transradial catheterization methods and devices used in said methods. In particular, the invention concerns a method of obtaining patent hemostasis of the radial artery by compressing the un-instrumented ulnar artery to increase radial artery flow while applying pressure to the radial artery access site. The invention further concerns a device for applying blunt pressure to the ulnar artery, and a method of use.

b. Description of Related Art

Radial artery instrumentation is becoming increasingly prevalent with cardiovascular procedures performed via transradial access, providing improvement in outcomes, cost, as well as comfort. Radial artery occlusion refers to the blockage of the radial artery. Radial artery occlusion is a consequence of radial artery cannulation, which obliterates the radial artery lumen, making it not available for access in the future.

After instrumentation, it is necessary to compress the radial artery at the access site to obtain hemostasis of the cannulation wound. The cannulation wound is an opening of the wall of the radial artery. Hemostasis of the cannulation (or sheath) wound is accomplished by applying blunt pressure to the radial artery at the cannulation wound site, or access site. The application of this blunt pressure on the radial artery often causes the artery to occlude or close, thereby denying bloodflow further downstream within the radial artery. Maintaining blood flow in the radial artery while compressing the access site, after instrumentation, reduces the risk of post-instrumentation radial artery occlusion. Patent hemostasis is therefore understood to mean achieving the cessation of bleeding at the cannulation wound (access site) of the radial artery, while blood is allowed to flow through the artery.

The following references are representative of the field pertaining to the present invention:

For example, U.S. Pat. No. 6,355,026 to Mick describes Right and left coronary catheters that are designed to be used in a transradial coronary catheterization. Also discussed are methods of inserting the catheters into a right or left coronary artery by a transradial approach.

In an article entitled Efficacy and Safety of Transient Ulnar Artery Compression to Recanalize Acute Radial Artery Occlusion After Transradial Catheterization (Am J Cardiol 2011; 107:1698-1701) Ivo Bernat, MD, and others, discuss a method directed to open an occluded radial artery after the radial artery becomes occluded. In the case of radial artery occlusion, 3-4 hours after hemostasis of the radial artery, ulnar artery compression was applied to attempt recanalization of radial artery. Bernat et. al. verified reopening of the radial artery by administration of heparin and compression of the ulnar artery.

SUMMARY OF INVENTION

A present invention method of catheterization of the radial artery directed at minimizing occurrences of radial artery occlusion is disclosed. The method comprises inserting a sheath into the radial artery of a patient at an access site. The desired catheterization procedure is then performed using the sheath to access the radial artery. Once the catheterization procedure is complete, an ulnar pressure is applied to the homolateral ulnar artery at an ulnar pressure site while the sheath remains inserted in the radial artery. The sheath is then removed from the radial artery while maintaining the ulnar pressure to the ulnar artery. Once the sheath is removed, and while continuing to apply the ulnar pressure, pressure is applied to the radial artery at the access site to obtain hemostasis at the access site.

In a preferred embodiment, the step of "applying a pressure to the radial artery at the access site to obtain hemostasis at the access site" is accomplished while maintaining the ulnar pressure to the ulnar artery.

In an embodiment of the present invention, a further step includes confirming that the step of applying ulnar pressure has reduced blood flow through the ulnar artery by monitoring flow of the ulnar artery prior to and after applying the ulnar pressure. In a further embodiment, monitoring flow of the ulnar artery includes sensing skin blood flow and/or pulsation at a fingertip or other location downstream of the ulnar pressure site. Digital plethysmography is employed in a preferred embodiment.

In another embodiment, the method further includes confirming patency of the radial artery during the step of applying a pressure to the radial artery by sensing skin blood flow and/or pulsation at a fingertip or other location downstream of the access site. In this embodiment, the sensing is performed while the ulnar artery is fully compressed (allowing no flow through the ulnar artery) and/or partially compressed (allowing less flow than when not compressed at all). Patency is confirmed, in an embodiment, by obtaining a metric relating to the sensing and comparing the metric with a standard metric for the patient, or with a previously-sensed metric. Preferably, the previously sensed metric is read after the applying the ulnar pressure step and before the step of removing the sheath from the radial artery. Digital plethysmography is employed in a preferred embodiment.

In an embodiment of the present invention method, the step of compressing the ulnar artery includes: providing an ulnar impinger, securing the ulnar impinger over the wrist such that the impinger contacts a first location over the ulnar artery, and activating the impinger to press on the ulnar artery at the first location.

In a preferred embodiment of the present invention, the step of compressing the ulnar artery includes: providing an ulnar impingement band having an inflatable bladder, securing the ulnar impingement band over the wrist such that the bladder contacts a first location over the ulnar artery, and inflating the bladder to impinge upon the ulnar artery at the first location.

There is further disclosed a device for use in applying a compressing force to the ulnar artery of a patient. The device includes a trunk having an inflatable bladder. The trunk is defined by a lower portion and an upper portion. The bladder is defined by an expandable envelopment existing between the lower portion and the upper portion. A pair of limbs are connected to and extend from the upper portion of the trunk.

Together, the pair of limbs and the trunk form a general Y-shape. A first limb of the pair of limbs is adapted to lay across the palm of a hand, between the thumb and the index finger and connect to the trunk to secure the first limb to the trunk and to secure the bladder to a portion of the patient's wrist corresponding with a first location over the ulnar artery. A second limb of the pair of limbs is adapted to lay over the wrist/distal forearm and connect to the trunk. This is to secure the second limb to the trunk and to further secure the bladder to the first location over the ulnar artery. One or more connectors are utilized for fixing the pair of limbs to the trunk.

In use, the bladder is located at the first location over the ulnar artery, and the pair of limbs are fixed around the hand and wrist to the trunk with the connectors. The bladder is inflated with a tube connected to an inflator to cause the bladder to impinge upon the ulnar artery at the first location.

There is further disclosed a device for use in applying a compressing force to the ulnar artery of a patient. The device comprises a trunk having an impinger. The trunk is defined by a lower portion and an upper portion. The impinger is defined by any device sufficient to apply a compression force. A pair of limbs are connected to and extend from the upper portion of the trunk. The pair of limbs together with the trunk form a general Y-shape. A first limb of the pair of limbs is adapted to lay across the palm of a hand, between the thumb and the index finger. The first limb connects to the trunk to secure the first limb to the trunk, and also to secure the impinger to a portion of the patient's wrist corresponding with a first location over the ulnar artery. A second limb of the pair of limbs is adapted to lay over the wrist/distal forearm and connect to the trunk to secure the second limb to the trunk and to further secure the bladder to the first location over the ulnar artery. One or more connectors are employed to fix the pair of limbs to the trunk. In use, the impinger is located at the first location over the ulnar artery. The pair of limbs are fixed around the hand and wrist to the trunk with the connectors. The impinger is activated to cause the bladder to impinge upon the ulnar artery at the first location.

Additional features, advantages, and embodiments of the invention may be set forth or are apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE EMBODIMENTS

The invention is directed to a method of obtaining patent hemostasis of the radial artery by compressing the un-instrumented ulnar artery to increase radial artery flow while applying pressure to the radial artery access site. The invention further concerns a device for applying blunt pressure to the ulnar artery, and a method of use.

Figure 1:
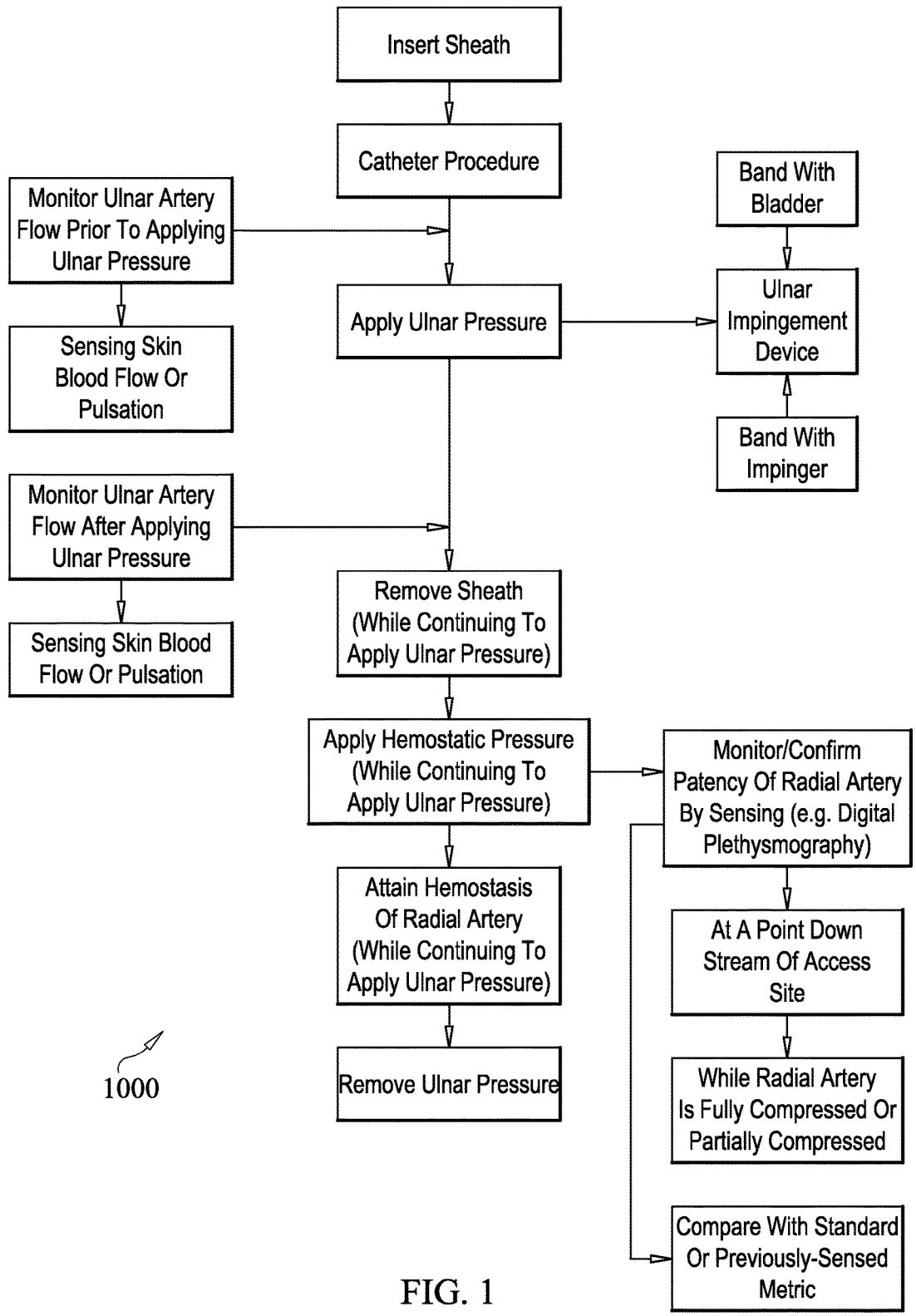
FIG. 1 is schematic layout of methods disclosed herein.
Figure 2:
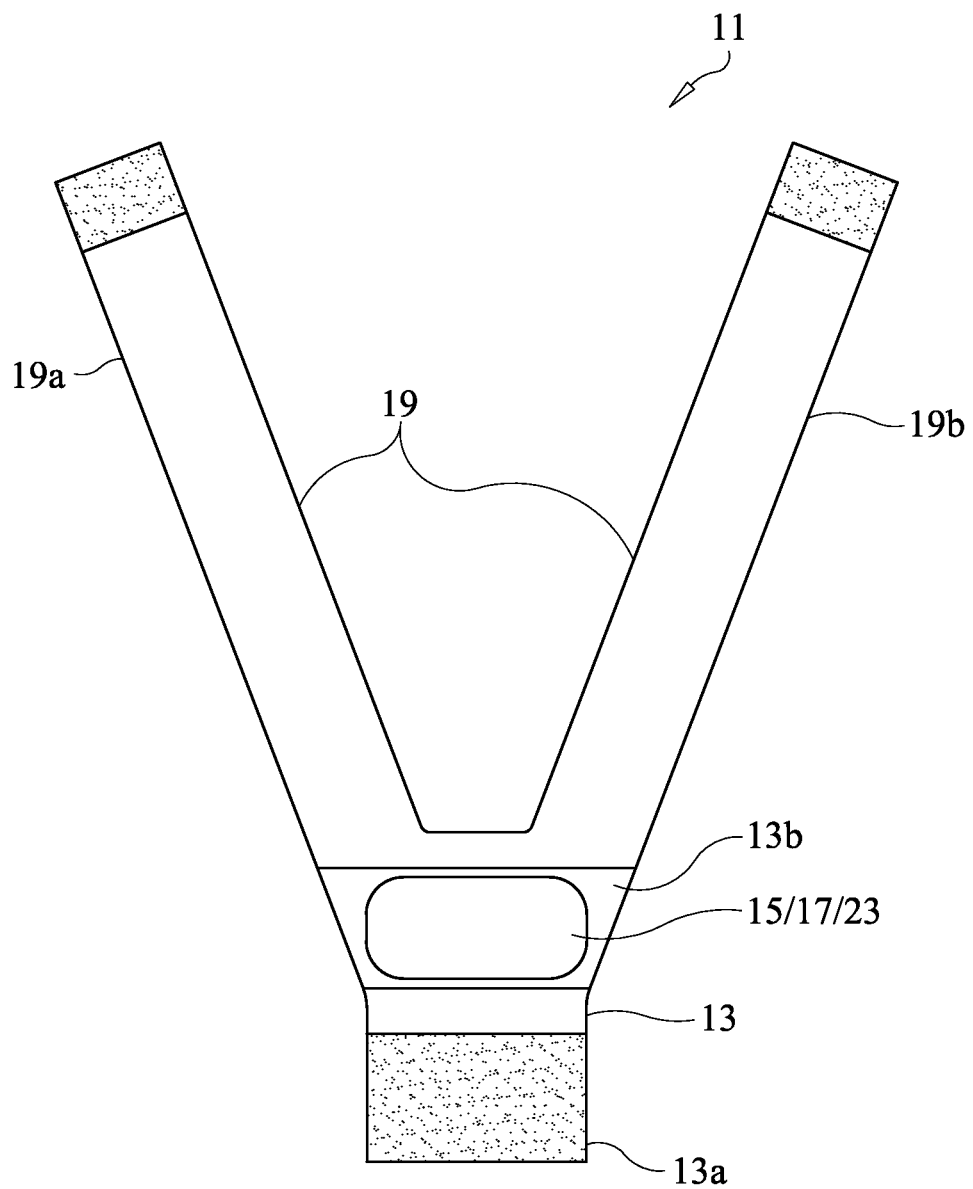
FIG. 2 is a plan view of the ulnar impingement device according to an embodiment of the present invention.
Figure 3:
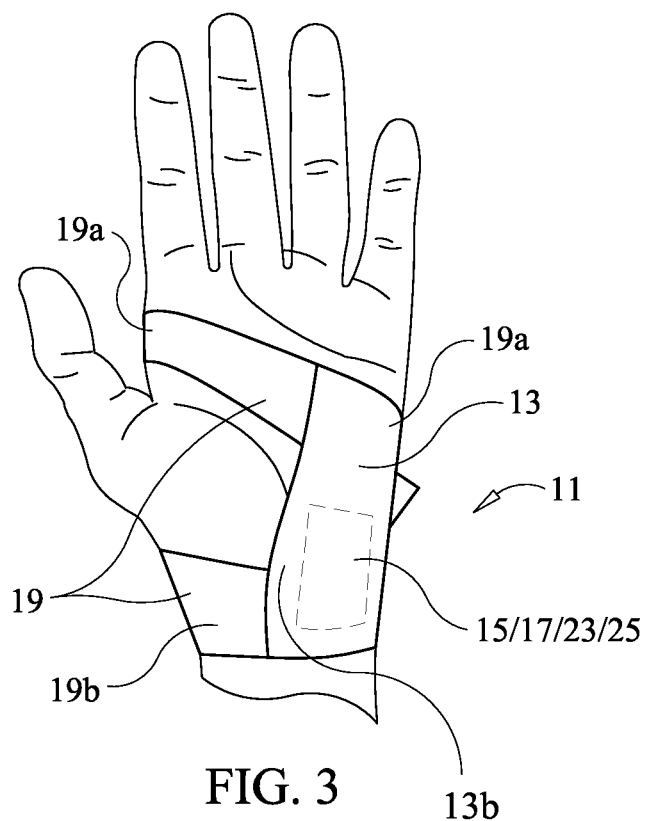
FIG. 3 is a view showing the ulnar impingement device applied to a patient according to an embodiment of the present invention.
Figure 4:
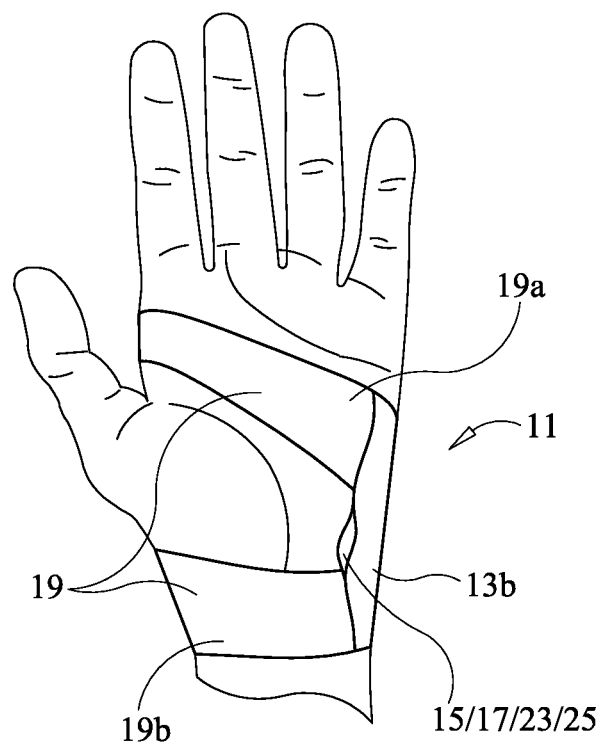
FIG. 4 is another view showing the bladder or impinger of the ulnar impingement device applied to a patient according to an embodiment of the present invention.
Figure 5:
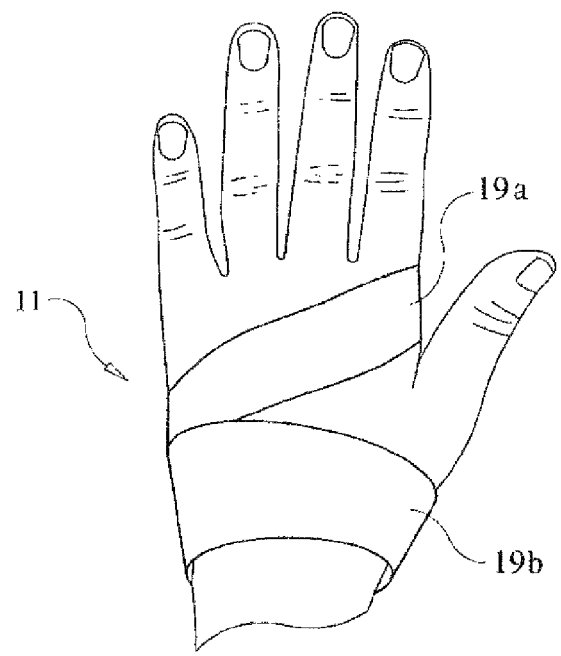
FIG. 5 is a view showing the ulnar impingement device applied to a patient showing the top of the hand according to an embodiment of the present invention.
Figure 6:
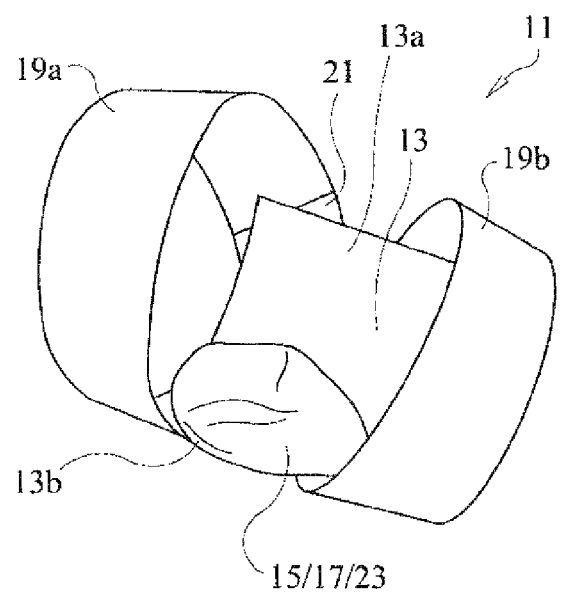
FIG. 6 is an isometric view of the ulnar impingement device shown with trunk fastened to the pair of limbs.

A present invention method of catheterization of the radial artery directed at minimizing occurrences of radial artery occlusion is disclosed. Referring to FIG. 1 specifically, and the Figures in general, the method 1000 comprises inserting a sheath into the radial artery of a patient at an access site. A sheath, as disclosed herein, is understood to encompass any device inserted into the radial artery and used to permit the access of instrumentation into the radial artery. The desired catheterization procedure is then performed using the sheath to provide instrumentation access the radial artery.

Once the catheterization procedure is complete, an ulnar pressure is applied to the homolateral ulnar artery at an ulnar pressure site while the sheath remains inserted in the radial artery. The sheath is then removed from the radial artery while maintaining the first pressure to the ulnar artery. Once the sheath is removed, and while continuing to apply the ulnar pressure, pressure is applied to the radial artery at the access site to obtain hemostasis at the access site.

In a preferred embodiment, the step of "applying a pressure to the radial artery at the access site to obtain hemostasis at the access site" is accomplished while maintaining the first pressure to the ulnar artery.

The radial artery and the ulnar artery are the two conduits for the flow of oxygenated blood to the hand. The arteries are interconnected and therefore form an interdependent flow network. When flow is reduced in one of the arteries, by compression for example, flow increases in the other artery. When the ulnar artery is compressed, flow in the ulnar artery is reduced, which causes an increase in pressure and flow in the radial artery.

In an embodiment, a further step includes confirming that the application of ulnar pressure has reduced blood flow through the ulnar artery. This is done by monitoring flow of the ulnar artery prior to and after applying the ulnar pressure. In a further embodiment, monitoring flow of the ulnar artery includes sensing skin blood flow and/or pulsation at a fingertip or other location downstream of the ulnar pressure site. Digital plethysmography is employed in one embodiment.

In another embodiment, the method 1000 further includes confirming patency of the radial artery during the step of applying a pressure to the radial artery. In a preferred embodiment, patency is accomplished by sensing skin blood flow and/or pulsation at a fingertip or other location downstream of the access site. Other sensing locations both upstream and downstream may be used to confirm patency of the radial artery. In the preferred embodiment, the sensing is performed while the ulnar artery is fully compressed (allowing no flow through the ulnar artery) and/or partially compressed (allowing less flow than when not compressed at all). Patency is confirmed, in an embodiment, by obtaining a metric relating to the sensing and comparing the metric with a standard metric for the patient, or with a previously-sensed metric. Metric is understood to mean a sensible, quantifiable value or reading, relating to the characteristic sensed. Preferably, the previously sensed metric is read after the applying the ulnar pressure step and before the step of removing the sheath from the radial artery. Digital plethysmography is employed, in a preferred embodiment, to obtain the metrics. Other sensing modes may be employed, so long as the selected mode is capable of confirming patency in one form or another.

In an embodiment of the present invention method 1000, the step of compressing the ulnar artery includes: providing an ulnar impinger, securing the ulnar impinger over the wrist such that the impinger contacts a first location over the ulnar artery, and activating the impinger to press on the ulnar artery at the first location. In a preferred embodiment, the first location is over the Guyon's canal, demarcated by pisiform bone on the medial aspect, directly over the ulnar artery pulse.

Impinger is understood to include any device capable of applying a force to the ulnar artery, whether alone or part of a system, sufficient to compress the ulnar artery. One exemplary class includes mechanical devices that expand in size to cause a band surrounding the wrist to constrict an object to compress the ulnar artery. Another exemplary class of impingers includes mechanical devices that constrict a band worn around the wrist sufficient to cause an object to press on the ulnar artery.

In a preferred embodiment, the step of compressing the ulnar artery includes: providing an ulnar impingement band having an inflatable bladder, securing the ulnar impingement band over the wrist such that the bladder contacts a first location over the ulnar artery, and inflating the bladder to impinge upon the ulnar artery at the first location.

Turning to the Figures generally, and particularly FIGS. 2-6, there is further disclosed a device 11 for use in applying a compressing force to the ulnar artery of a patient. The device 11 includes a trunk 13 having an inflatable bladder 15. The trunk 13 is defined by a lower portion 13a and an upper portion 13b. The bladder 15 is defined by an envelopment 17 existing between the lower portion 13a and the upper portion 13b. A pair of limbs 19 are connected to and extend from the upper portion 13b of the trunk 13. Together, the pair of limbs 19 and the trunk 13 form a general Y-shape. Preferably, the pair of limbs 19 and the trunk 13 are planar and form a Y-shape band. A first limb 19a of the pair of limbs 19 is adapted to lay across the palm of a hand, between the thumb and the index finger. The first limb 19a is adapted to connect to the trunk 13 for securing the first limb 19a to the trunk 13 and for securing the bladder 15 to a portion of the patient's wrist corresponding with a first location 25 over the ulnar artery. A second limb 19b of the pair of limbs 19 is adapted to lay over the wrist/distal forearm and connect to the trunk 13. This is to secure the second limb 19b to the trunk 13 and to further secure the bladder 15 to the first location 25 over the ulnar artery. One or more connectors 21 are utilized for fixing the pair of limbs 19 to the trunk 13. In a preferred embodiment, the connector is Velcro.

In use, the bladder 15 is located at the first location 25 over the ulnar artery, and the pair of limbs 19 are fixed around the hand and wrist to the trunk 13 with the connectors 21. The bladder 15 is inflated with a tube connected to an inflator to cause the bladder 15 to impinge upon the ulnar artery at the first location 25.

There is further disclosed a device 13 for use in applying a compressing force to the ulnar artery of a patient. The device 13 comprises a trunk 13 having an impinger 23. The trunk 13 is defined by a lower portion 13a and an upper portion 13b. The impinger 23 is defined by any device sufficient to apply a compression force. Examples include expanding springs, expanding screw-type appurtenances, or other devices and systems as discussed herein. A pair of limbs 19 are connected to and extend from the upper portion 13b of the trunk 13. The pair of limbs 19 together with the trunk 13 form a general Y-shape. A first limb 19a of the pair of limbs 19 is adapted to lay across the palm of a hand, between the thumb and the index finger. The first limb 19a connects to the trunk 13 to secure the first limb 19a to the trunk 13, and also to secure the impinger 23 to a portion of the patient's wrist corresponding with a first location 25 over the ulnar artery. A second limb 19b of the pair of limbs 19 is adapted to lay over the wrist/distal forearm and connect to the trunk 13 to secure the second limb 19b to the trunk 13 and to further secure the impinge 23 to the first location over the ulnar artery. One or more connectors 21 are employed to fix the pair of limbs 19 to the trunk 13. In use, the impinger 23 is located at the first location 25 over the ulnar artery. The pair of limbs 19 are fixed around the hand and wrist to the trunk 13 with the connectors 21. The impinger 23 is activated to cause the impinger 23 to impinge upon the ulnar artery at the first location 25.

The invention claimed is:

1. A method of obtaining hemostasis of a radial artery of a patient after performing a catheterization procedure at an access site of the radial artery, comprising performing the following steps:
   (a) continuously applying a hemostatic pressure to the radial artery at the access site;
   (b) continuously applying an ulnar pressure to an ulnar artery at an ulnar pressure site, wherein the ulnar pressure only partially compresses the ulnar artery;
   (c) maintaining simultaneously the hemostatic pressure and the ulnar pressure at least until hemostasis of the radial artery is achieved.

2. The method of claim 1, further comprising means for applying the ulnar pressure to the ulnar artery.

3. The method of claim 1, wherein the ulnar pressure site is a Guyon's canal.

4. The method of claim 1, further comprising monitoring patency of the radial artery by sensing.

5. The method of claim 4, further comprising the step of confirming patency of the radial artery while the hemostatic pressure to the radial artery is being continuously applied.

6. The method of claim 1, wherein the ulnar pressure only partially compressing the ulnar artery thereby allows less flow through the ulnar artery than when the ulnar artery is not compressed at all.

7. The method of claim 1 further comprising the step of removing the ulnar pressure to the ulnar artery.

8. The method of claim 7 wherein the step of removing the ulnar pressure to the ulnar artery is performed after hemostasis of the radial artery is achieved.

9. The method of claim 1, wherein applying the ulnar pressure to the ulnar artery comprises: providing an ulnar impinger, securing the ulnar impinger over a wrist such that the impinger contacts the ulnar pressure site, and activating the impinger to press on the ulnar artery at the ulnar pressure site.

10. The method of claim 1, wherein applying the ulnar pressure to the ulnar artery comprises: providing a band having an inflatable bladder, securing the band over a wrist such that the bladder contacts the ulnar pressure site, and inflating the bladder to compress the ulnar artery at the ulnar pressure site.

11. The method of claim 5, wherein the step of confirming patency further comprises using digital plethysmography.

12. The method of claim 4, wherein the sensing is performed upstream or downstream of the access site.

13. The method of claim 9, wherein the ulnar impinger comprises of a mechanical device with a constricting band worn around the wrist sufficient to cause an object to press on the ulnar artery.

14. A method of catheterization of a radial artery of a patient, directed at minimizing occurrences of radial artery occlusion, comprising the steps of: (a) inserting a sheath into the radial artery at an access site; (b) performing a catheterization procedure using the sheath to access the radial artery; (c) continuously applying a first pressure to an ulnar artery at an ulnar pressure site, wherein the first pressure only partially compresses the ulnar artery; (d) removing the sheath from the radial artery; (e) continuously applying a second pressure to the radial artery at the access site and (f) maintaining simultaneously the first pressure and the second pressure at least until hemostasis of the radial artery is achieved.

15. The method of claim 14 wherein the step of applying the first pressure to the ulnar artery is performed while the sheath remains inserted in the radial artery.

16. The method of claim 14 wherein the step of removing the sheath from the radial artery is performed while maintaining the first pressure to the ulnar artery.

17. The method of claim 14, further comprising the step of: monitoring and/or confirming patency of the radial artery during the step of continuously applying the second pressure to the radial artery, by sensing skin blood flow and/or pulsation at a fingertip or other location downstream of the access site.

* * * * *